(12) United States Patent
Gao et al.

(10) Patent No.: US 8,410,027 B2
(45) Date of Patent: Apr. 2, 2013

(54) DENSITY MODIFICATION IN ARRAYS OF SURFACE-ATTACHED NUCLEIC ACID MOLECULES

(75) Inventors: Yuan Gao, Mountain View, CA (US); Wei Wang, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 13/023,805

(22) Filed: Feb. 9, 2011

(65) Prior Publication Data

US 2011/0136694 A1    Jun. 9, 2011

Related U.S. Application Data

(62) Division of application No. 12/217,087, filed on Jun. 30, 2008, now abandoned.

(51) Int. Cl.
*C40B 40/06* (2006.01)
(52) U.S. Cl. .......................................... 506/16
(58) Field of Classification Search .................. None
See application file for complete search history.

(56) References Cited

PUBLICATIONS

Benters et. al. (Jan. 2002) Nucleic Acids Research vol. 30 article e10 pp. 1 to 7.*
Immoos et al. (Aug. 17, 2004) Journal of the American Chemical Society vol. 126 pp. 10814 to 10815.*
Fedurco et al. (Feb. 9, 2006) Nucleic Acids Research vol. 34 pp. 1 to 13.*

* cited by examiner

*Primary Examiner* — Ardin Marschel
*Assistant Examiner* — Christian Boesen

(57) ABSTRACT

Substrates having nucleic acid polymers attached at varying surface densities and methods for creating substrates having nucleic acid polymers attached at varying surface densities are provided. Methods according to embodiments of the invention are adapted to the rapid synthesis of arrays of DNA polymers on a substrate surface. In embodiments of the invention an array of DNA molecules on a substrate comprises a plurality of DNA polymers attached to a trifunctional linker such that at least two DNA polymers are attached to one trifunctional linker that is attached to the surface of the substrate. By coupling trifunctional linkers to trifunctional linkers that are attached to a substrate surface, the density of DNA polymers on a substrate surface is increased.

14 Claims, 8 Drawing Sheets

DENSITY MODIFICATION IN ARRAYS OF SURFACE-ATTACHED NUCLEIC ACID MOLECULES

CROSS REFERENCE TO RELATED APPLICATIONS

This application is a Divisional of U.S. patent application Ser. No. 12/217,087, entitled "Density Modification in Arrays of Surface-Attached Nucleic Acid Molecules," filed Jun. 30, 2008, now pending, and is related to U.S. patent application Ser. No. 11/646,602, entitled "Method and Apparatus for Combined Electrochemical Synthesis and Detection of Analytes," filed Dec. 28, 2006, now pending, U.S. patent application Ser. No. 11/646,615, entitled "Method and Apparatus for Match Quality Analysis of Analyte Binding," filed Dec. 28, 2006, now pending, and U.S. patent application Ser. No. 11/646,600, entitled "Quality Control Methods for the Manufacture of Polymer Arrays" filed Dec. 28, 2006, now pending, the disclosures of which are considered part or and are incorporated by reference in the disclosure of this application.

BACKGROUND OF THE INVENTION

1. Field of the Invention

The embodiments of the present invention relate to arrays of polymers on the surface of a substrate, and more particularly to arrays of polymers having varied surface densities, to arrays of nucleic acid polymers, and to methods of making arrays of nucleic acid polymers having varied surface densities.

2. Background Information

Microarrays of nucleic acids, peptides, proteins, and oligosaccharides continue to gain importance as powerful tools for research and diagnostic applications in the biomedical sciences. Nucleic acid microarrays, for example, can be used to monitor gene expression and genetic mutations in a massively parallel manner. Proteinaceous microarrays provide the ability, for example, to characterize the molecular progression of disease, research cellular pathways, and perform high throughput screening in drug discovery applications. The ability to collect large volumes of information is an integral part of biomarker discovery and personalization of medical treatments. Further, other applications in bioscience, such as for example, the analysis of the proteomic content of an organism, disease detection, pathogen detection, environmental protection, food safety, and biodefense are capable of benefiting from tools that allow rapid multiplexed interrogation of analyte samples.

Genetic information in living organisms is contained in the form of very long nucleic acid molecules such as deoxyribonucleic acid (DNA) and ribonucleic acid (RNA). Naturally occurring DNA and RNA molecules are typically composed of repeating chemical building blocks called nucleotides which are in turn made up of a sugar (deoxyribose or ribose, respectively), a phosphate group, and one of five bases, adenine (A), cytosine (C), guanine (G), and thymine (T) or uracil (U). The human genome, for example, contains approximately three billion nucleotides of DNA sequence and an estimated 20,000 to 25,000 genes. DNA sequence information can be used to determine multiple characteristics of an individual as well as the presence of and or suceptibility to many common diseases, such as cancer, cystic fibrosis, and sickle cell anemia.

As the genomic and proteomic knowledge base expands, so does the need for methods to collect, understand, and apply biologically relevant information. The drive towards personalized medicine magnifies these needs. Methods, such as analyses using microarrays that allow the use of small volumes of sample for highly multiplexed analysis of a plurality of components are valuable tools. Methods that provide for the controllable automated manufacture of arrays derive value from these same biomedical detection and analysis goals.

DETAILED DESCRIPTION OF THE INVENTION

Embodiments of the invention are directed to methods for modifying the density of polymers attached to the surface of a substrate and to the resulting substrate having polymers attached to its surface. Methods according to embodiments of the invention are useful for making arrays of polymers on a substrate. The ability to control the density of polymers on the surface of a substrate allows, for example, for enhancing signal to noise ratio in situations in which the presence of the polymer and or the binding of a second molecule to the polymer is to be detected. Increased density provides increased signal for detection which is especially useful when surface chemistry is detected electronically. Further, for example, a substrate having regions in which polymers are provided at different densities allows for the ability to perform concentration-based assays.

DNA hybridization is used in micro-array based techniques for DNA analysis and detection. Embodiments of the invention enable production of DNA microarrays in which the surface densities of immobilized DNA probes can be directly compared and optimized on the same chip for the capture of different target molecules. Additionally, embodiments of the invention provide for spacing the DNA probes above the surface of the substrate to reduce steric constraints imposed by the surface of the substrate and improve hybridization efficiencies.

Figure 1:
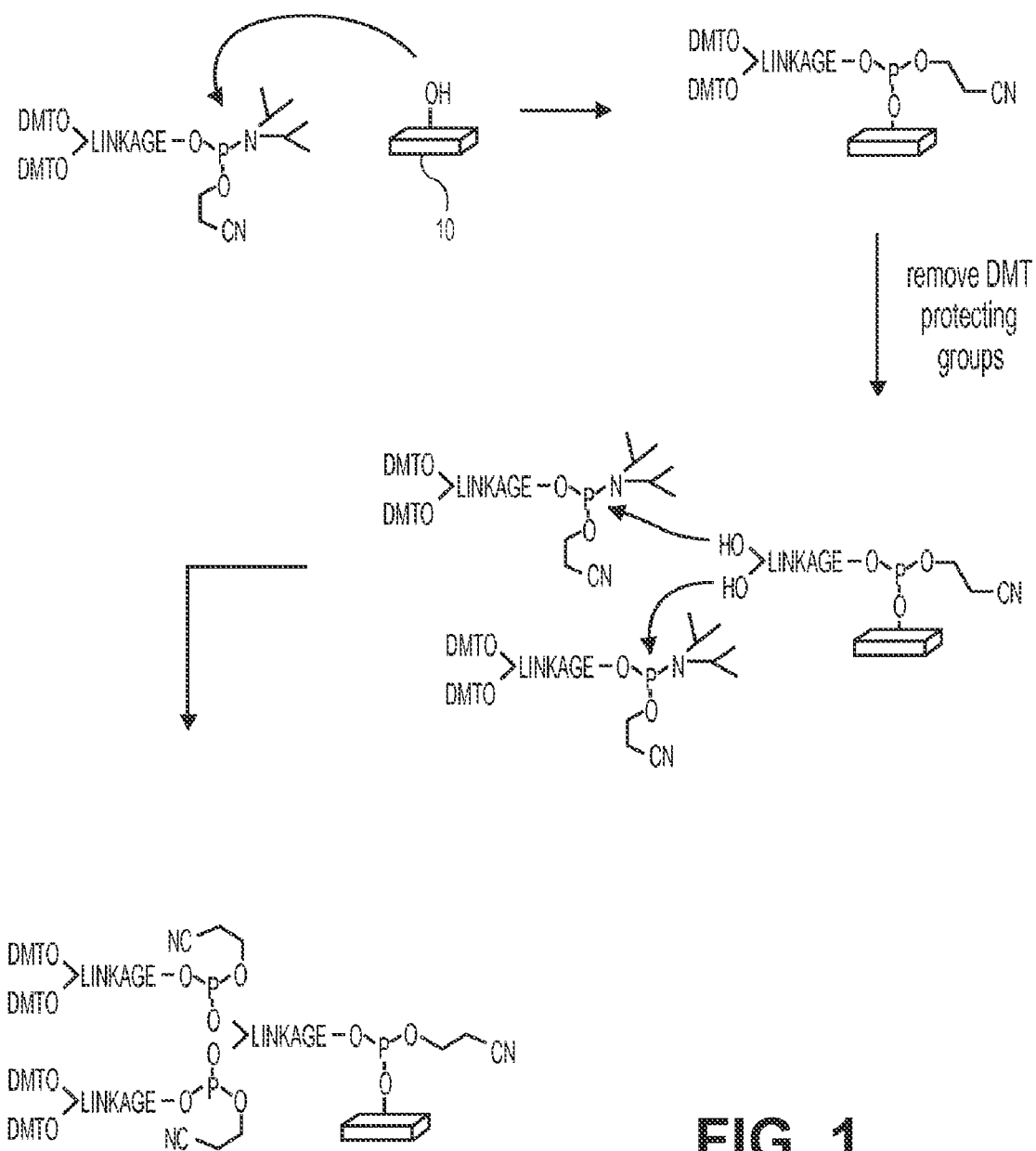
FIG. 1 schematically diagrams a surface chemistry methodology that allows for the controllable modification of the density of polymers attached to the surface of a substrate.

FIG. 1 provides an exemplary scheme for modifying polymer density on a substrate surface. In this example, the substrate surface provides hydroxyl groups (—OH) for molecular attachment. The substrate may be, for example, a glass, a silicon, a metal, or other surface (or combination thereof) as described more fully herein. Optionally, the substrate may be modified in order to provide an available hydroxyl for molecular attachment, according to well known techniques, such as silanation, oxidation, or coating, and as described more fully herein. Other protecting groups, linkers, trifunctional linkers, and arrangements of building blocks are possible as described more fully herein. In FIG. 1, a trifunctional molecular building block having two DMT (dimethoxytrityl) protected hydroxyl groups and a phosphoramidite functional group is reacted with a surface attached —OH group of substrate 10. The trifunctional linking molecule has a functional end for linking to the substrate and two additional functional ends for attaching desired polymers to the surface of the substrate. The resulting substrate has an attached building block capable of providing two hydroxyl groups (—OH) for further molecular attachment. The linkage between the phosphoramidite and the DMT-protected hydroxyls is, for example, an alkyl or aromatic structure, such as a hydrocarbon chain or ring, a sugar structure, or a phenyl or diphenyl. The DMT protecting group is removed by adding an organic acid such as trichloroacetic acid or dichloroacetic acid in methylenedichloride, an inorganic acid, or an electrogenerated or photogenerated acid (EGA or PGA, respectively) to provide an —OH group for further molecular attachment. In this way, surfaces can be created having an increased number of hydroxyl groups available for further molecular attachment.

Figure 2:
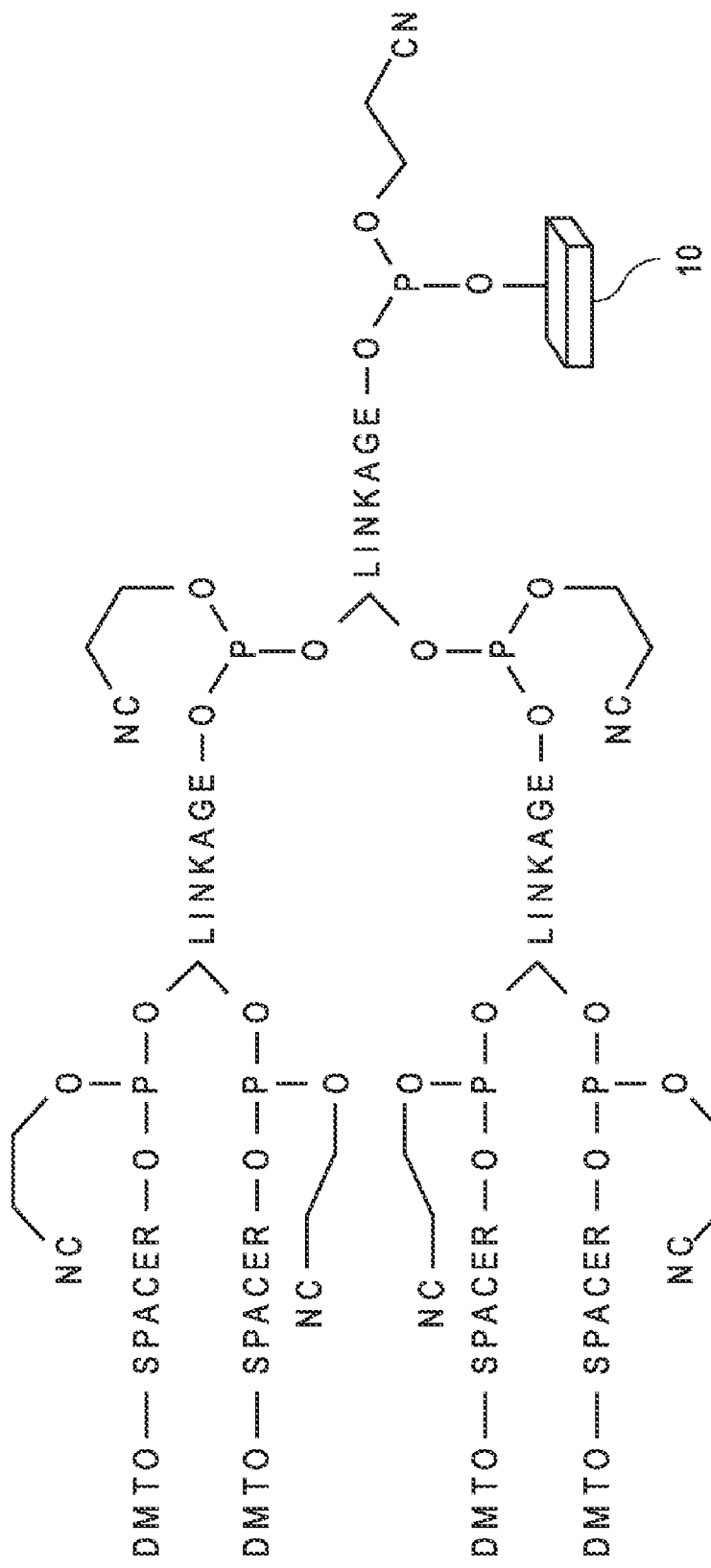
FIG. 2 diagrams an alternate example in which a spacer molecule has been included in the example shown in FIG. 1.

In an optional further coupling reaction, the DMT protecting groups are removed from the molecule (using an acid) in FIG. 1, and two trifunctional linker molecules are coupled to the deprotected hydroxyl groups creating a structure having four sites for further molecular coupling that are protected by DMT protecting groups, as shown in FIG. 2. By the coupling of multiple linker molecules to a single surface-attachment site, surfaces can be created having an increased number of hydroxyl groups available for further molecular attachment. This methodology allows the creation of surfaces having a controllable number of attachment sites for functional polymers.

In FIG. 2, a molecule capable of providing multiple attachment sites for desired molecules is attached through one attachment point to substrate 10. Two additional trifunctional linker molecules are coupled to the first trifunctional linker molecule that is attached to the surface of the substrate. In this example, spacer groups are added to the trifunctional linker molecule and the spacer group is attached to the trifunctional linker through an optional phosphate group. For optical detection and fluorescent assays, the spacer molecule can function to reduce undesired self-quenching or signal reduction that occurs through the interaction of closely spaced label molecules (interactions such as, for example, through energy transfer processes that occur in the place of fluorescent emissions). Spacing a probe molecule further from the surface of the substrate to which it is attached can also function to increase the probe molecule's ability to bind to target analytes by reducing steric constraints imposed by the surface and neighboring molecules that are themselves attached to the surface of the substrate.

Figure 3A:
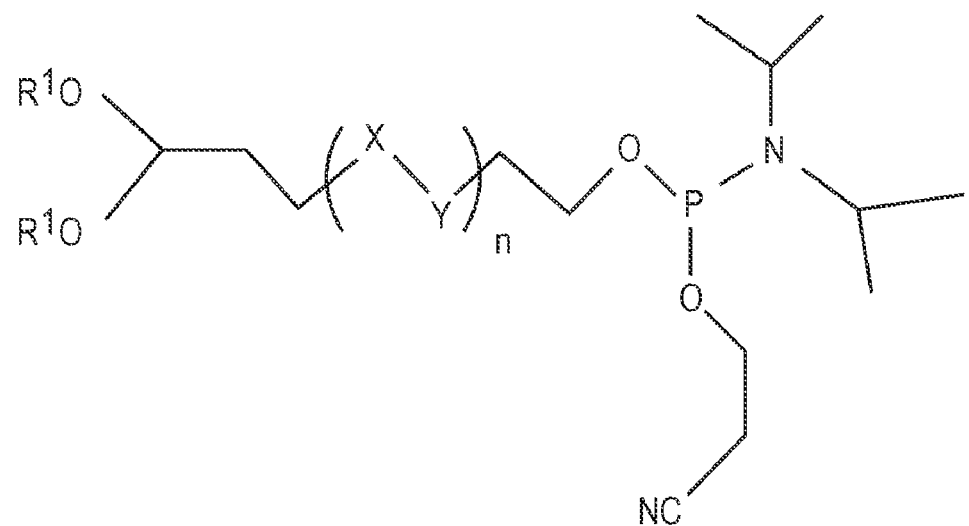
FIG. 3A provides further exemplary trifunctional linker molecules and FIG. 3B provides exemplary spacer molecules.

FIG. 3A diagrams a trifunctional linker molecule useful in embodiments of the present invention for increasing and or controlling the density of polymers attached to a substrate surface. In the example of FIG. 3A, $R^1$ represents a protecting group, such as, for example a DMT group, or another protecting group as is know in the art or described herein. The functional group $R^1$ can be the same group or a different group for the two instances in which $R^1$ appears in the molecule of FIG. 3A. The $R^1$ group is removed and a DNA polymer is attached or built onto the deprotected arm of the trifunctional linker. The functional groups X and Y can be the same or different and can be a $CH_2$, a $CHR^2$, $CR^2R^3$, an O, an S, a NH, or a $NR^3$. In the case where X (or Y) is an O, a NH, or a S, or a $NR^3$, then the functional groups X and Y are not the same, and then Y (or X) is a $CH_2$, or a $CHR^2$. The functional group $R^2$ can be —OH, —$NH_2$, —$CH_3$, —$CH_2OH$, —$CH_2CH_3$, —$CH_2CH_2OH$, or other alkane or alkene having from 3 to 7 carbon atoms and from 0 to 4 oxygen atoms. The functional group $R^3$ can be —$CH_3$, —$CH_2CH_3$, or other alkane having from 3 to 5 carbon atoms. The value for "n" in FIG. 3A is from 0 to 10. In alternate embodiments, the X-Y of FIG. 3A is replaced by a phenyl or diphenyl or a sugar having 5 or 6 atom chain length or ring (a pentose, hexose, or heptose molecule). The phosphoramidite functional group facilitates coupling of the phosphate group to a surface-attached hydroxyl group.

Figure 3B:
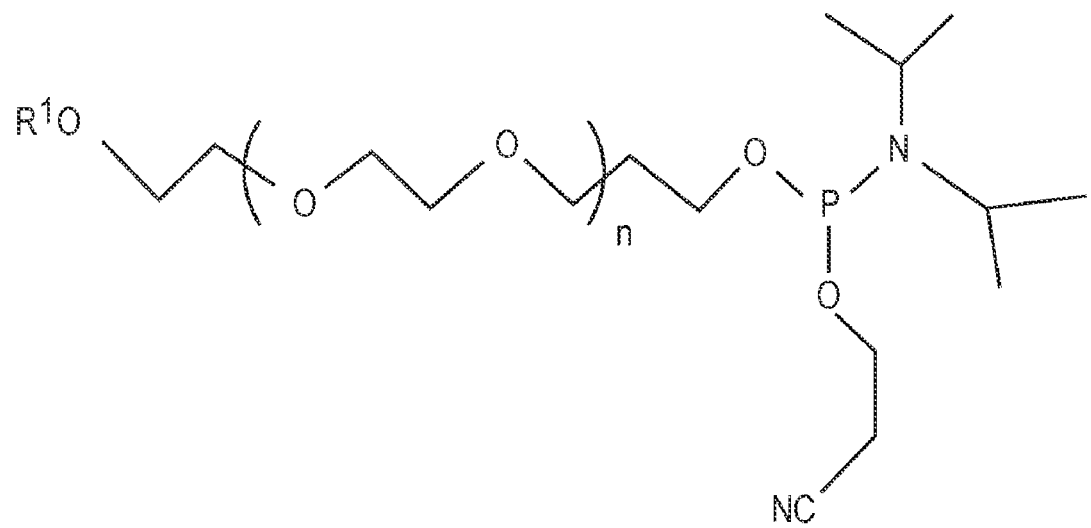

FIG. 3B diagrams an exemplary spacer group that can be used in embodiments of the invention. In the example of FIG. 4A, $R^1$ represents a protecting group, such as, for example a DMT group, or another protecting group as is know in the art or described herein. The value for "n" in FIG. 3B is from 0 to 10. The phosphoramidite functional group facilitates coupling of the phosphate group to a surface-attached hydroxyl group.

In FIGS. 1, 2, and 3A and 3B, the phosphorous of the phosphate group is shown as attached to a —$OCH_2CH_2CN$, however, other configurations are possible. For example, the —$OCH_2CH_2CN$ could be replaced by —$OCHR^1CHR^2CN$ or —$OCR^1R^2CR^1R^2CN$ where $R^1$ and $R^2$ are —$CH_3$, —$CH_2CH_3$, or other alkane having from 3 to 5 carbon atoms. The —$OCH_2CH_2CN$ group is shown here because it is typically used in solid phase DNA synthesis procedures.

Although exemplary structures are diagrammed in FIGS. 1 and 2, other molecular arrangements are possible. For example, the trifunctional linker molecule of FIG. 1 or 2 can be attached to a substrate surface through a spacer group as described by FIG. 3B or as described further herein. The trifunctional linker molecule of FIG. 1 may also have spacer molecules attached to the arms that are DNA attachment points such that spacer molecules are located between the DNA polymer and the trifunctional linker group. The resulting structure having two DNA molecules attached to one trifunctional linker that is attached to a substrate surface may optionally contain zero, one, two, or three spacer molecules. Similarly a structure having two trifunctional linker molecules attached to a third trifunctional linker that is attached to a surface (such as in FIG. 2) may optionally comprise one, two, three, or seven spacer molecules. In the example of three trifunctional linkers (such as in FIG. 2), the spacer molecules may be, for example, between the surface of the substrate and the first trifunctional linker, between the first trifunctional linker and the second and third trifunctional linkers, and or between the second and third trifunctional linkers and the DNA polymers. In one embodiment, the spacer molecule is located between the second (and third) trifunctional linker and the DMT protecting group (the site at which a DNA polymer will be attached) as shown in FIG. 2.

A spacer molecule typically is a molecule inserted into the growing polymer, inserted between a DNA molecule and a trifunctional linker, or inserted between the surface of the substrate and a trifunctional linker molecule that does not necessarily convey functionality to the a surface-attached probe or nucleic acid molecule, such as molecular recognition functionality, but instead elongates the distance between the substrate surface and the probe functionality to enhance the exposure (steric availability) of the probe functionality on the surface of the substrate. A spacer molecule has a chain length of 2 to 30 atoms and is comprised of C, H, O, S, N, and or P. The spacer molecules may be, for example, aryl acetylene, ethylene glycol oligomers containing 2-10 monomer units (PEGs), diamines, diacids, amino acids, and polypeptides and polymers of amino acid derivatives such as for example, amino hexanoic acids, and combinations thereof. Diamines are molecules of the general formula $NH_2RNH_2$, where R is a branched or unbranched hydrocarbon (a molecule composed of carbon and hydrogen) having from 2 to 25 carbon atoms, wherein one or more carbon atoms may be replaced by oxygen, sulfur, silicon, and or nitrogen atoms. Examples of diamines include ethylene diamine and diamino propane. Diacids are molecules of the general formula R'OOC—R"—COOR', where R' is a branched or unbranched hydrocarbon having from 2 to 25 carbon atoms, wherein one or more carbon atoms may be replaced by oxygen, sulfur, silicon, and or nitrogen atoms, and R' is H or a hydrocarbon having from 1 to 10 carbon atoms. Typically, the OR' groups are removed during the reactions to attach the spacer molecule to the substrate surface and attach the spacer molecule to the nascent polymer and the resulting linker molecule has the structure —CO—R"—CO—. Spacer groups may also comprise phosphates, such as in the example shown in FIG. 3B. Alternatively, the spacers may be the same molecule type as that being synthesized (i.e., nascent polymers), such as polynucleotides and oligonucleotides.

The molecule diagrammed in FIGS. 3A and 3B can be attached to a substrate surface through standard solid phase chemistry used in solid-phase DNA synthesis processes. The phosphoramidite group is coupled to an available hydroxyl group attached to a substrate surface. For example, molecules having a phosphoramidite group can be dissolved in a 5-ethylthio-1H-tetrazole solution in acetonitrile and incubated for 30 minutes at room temperature to couple the molecule to a substrate surface having available —OH groups for coupling.

In general, a trifunctional linker molecule is a molecule that is a branched or bifurcated molecule having three points for molecular attachment. Typically the molecule is capable of being attached to the substrate surface through one point and is capable of attaching to a polymer through two points of attachment. To the extent that the trifunctional linker has three functional arms it might also be described as a Y-shaped molecule or molecular building block, although unlike the Y, the three functional arms might be of different lengths and the Y-shape is a simplification that also does not necessarily capture the relative angles of the arms with respect to one another.

In general, a molecular chain length describes the number of atoms connected to each other along the longest chain of continuously connected atoms in the molecule.

In general, molecules shown in FIGS. 1, 2, and 3A and 3B, can be synthesized by transforming the hydroxyl into a phosphoramidite group using 2-cyanoethyl-N,N-diisopropylchlorophosphoramidite and diisopropylethylamine in THF (materials are commercially available, from for example, Sigma Aldrich, St. Louis, Mo.) at −78° C. to 25° C. Additionally, synthesis methods for trifunctional linkers can be found in, for example, "Fluorescence Enhancement through Enzymatic Cleavage of Internally Quenched Dendritic Peptides: A Sensitive Assay for the AspN Endoproteinase," *Angew. Chem.*, 41:3233 (2002) and "Dendrimers and Combinatorial Chemistry—Tools for Fluorescent Enhancement in Protease Assays," *Tetrahedron*, 60:8721 (2004) and references therein.

An array is an intentionally-created collection of molecules housed on a solid support in which the identity or source of a group of molecules is known based on its location on the array. The molecules housed on the array and within a feature of an array can be identical to or different from each other. A macroarray generally contains feature sizes of about 300 µm or larger and can be imaged by gel and blot scanners. A micro array generally has feature sizes of less than 300 µm.

The features, regions, spots, or sectors of an array may have any convenient shape, for example, circular, square, rectangular, elliptical, or wedge-shaped. In some embodiments, the region in which each distinct molecule is synthesized within a sector is smaller than about 1 mm$^2$ or less than 0.5 mm$^2$. In further embodiments the regions have an area less than about 10,000 µm$^2$ or less than 2.5 µm$^2$. Additionally, multiple copies of a polymer are located within any region. The number of copies of a polymer can be in the thousands to the millions within a region. In general, an array can have any number of features, and the number of features contained in an array may be selected to address such considerations as, for example, experimental objectives, information-gathering objectives, and cost effectiveness. An array could be, for example, a 20×20 matrix having 400 regions, 64×32 matrix having 2,048 regions, or a 640×320 array having 204,800 regions. Advantageously, the present invention is not limited to a particular size or configuration for the array.

A solid support, support, or substrate is an object having a rigid or semi-rigid surface or surfaces. In some aspects at least one surface of a solid support is planar or substantially planar. The features of an array optionally form synthesis regions that are for example, wells, depressions, raised regions, pins, or etched trenches. In embodiments of the invention the substrate comprises a silicon wafer or a portion of a silicon wafer. A silicon wafer may also be referred to as a chip or a semiconductor substrate. A wafer or chip may be fashioned in various shapes and sizes. The chip could be overlaid or embedded with circuitry for driving electrodes, sensing voltages, microprocessors, memory functions, and input/output capabilities. In embodiments of the invention, the chip comprises at least surface-accessible electrodes and embedded circuitry for driving the electrodes and sensing voltages. A substrate may also be comprised of silicon, glass, nylon, plastic or other polymeric material, silicon nitride, metals, metal oxides, metal nitrides, or combinations thereof.

Many substrate materials, such as metals, metal oxides, and SiO$_2$, have surface-attached —OH groups that are available for further reaction and molecular coupling. Further, surfaces that present —OH groups for molecular coupling can be created on substrate surfaces, through, for example, creating a thin oxide layer on a metal (such as through chemical or plasma etching processes) and depositing a thin layer of SiO$_2$ onto the surface. If the substrate surface is SiO$_2$, the surface has been coated with SiO$_2$, the surface is a metal having available —OH groups, molecules are optionally attached to the sensor surface through the use of silane linkers (or organo silane compounds). Silane linkers are molecules that have at least two different reactive groups bonded to the silane atom of the molecule: Y—R—Si—(X)$_2$. One of the reactive groups is capable of bonding to inorganic materials such as glass (SiO$_2$) and metals, the X group. These functional groups that are capable of bonding to inorganic materials are groups such as methoxy, ethoxy, chlorine, and silanolic hydroxyl groups. The second functional group is a group such as a vinyl, an epoxy, a methacryl, an amino, a mercapto, or a carboxylic acid group that is capable of forming a chemical bond to an organic material, the Y group. The R group is typically an organic group comprised of from 1 to 10 carbon atoms, such as a straight chain or branched alkane. For example, a silanating agent, such as hydroxypropyltriethoxysilane can be vapor deposited or supplied in a solution to the surface to be silanated. After reaction, the surface presents a —OH group for further molecular coupling. Metal surfaces such as nickel, palladium, platinum, titanium dioxide, aluminum oxide, indium tin oxide, copper, iridium, aluminum, titanium, tungsten, rhodium or other surface having available hydroxy groups or other similar surface groups can also be silanated for further attachment of molecules. A very thin layer of oxide can be created on a metal surface, for example, by etching the metal surface with an oxygen plasma or through damascene processes.

A probe or probe molecule is a small molecule or biomolecule capable of undergoing a binding or molecular recognition event with a target molecule. Molecular recognition is a specific interaction between molecules. Examples of molecular recognition events are receptor-ligand, antibody-antigen, sugar-lectin, DNA-protein, and nucleic acid hybridization reactions. A target or target molecule refers to a small molecule or biomolecule that is specifically recognized by a probe molecule through a molecular recognition event. In the case of nucleic acids, a molecular recognition event occurs when nucleic acids hybridize to complementary nucleic acids.

The length chosen for a nucleic acid to be used as a probe molecule in an assay (such as a hybridization assay) depends on several factors, including G/C content of the sequence, positioning of mismatched bases (if any), degree of uniqueness of the sequence as compared to the population of target nucleotides, the chemical nature of the polynucleotide (e.g., methylphosphonate backbone and phosphorothiolate), desired conditions for hybridization reaction (e.g., temperature and ionic strength of the solution). Typically a probe molecule will be at least 5 nucleotides and less than 75 nucleotides in length. Preferably the probe is between 24 and 60 nucleotides in length. Embodiments of the invention provide arrays of nucleic acids that are suitable for use as probe molecules to, for example, detect the presence of particular nucleic acid sequences in samples to be analyzed.

A hybridization reaction is a process in which two single-stranded polynucleotides bind and form a stable double-stranded polynucleotide. In a hybridization event complementary nucleic acid bases pair up, and an adenine (A) pairs with a cytosine (C), and a guanine (G) pairs with a thymine (T) or uracil (U) (through, for example, standard Watson-Crick hydrogen-bonding interactions). Depending on conditions of pH, temperature, salt concentration, nucleic acids that are not absolutely complementary are able to hybridize. In general, substantially complementary nucleic acids refer to nucleic acids that have 80% or greater complementary base pairing. Highly complementary nucleic acids refer to nucleic acids having 90% or greater complementary base pairing. The proportion of the population of polynucleotides that forms stable hybrids is referred to as the degree of hybridization. Hybridization refers to the formation of double stranded species between a probe polynucleotide and a target nucleic acid wherein the probe preferentially hybridizes target nucleic acids that are substantially complementary to the probe nucleic acid and does not hybridize nucleic acids that are not substantially complementary.

Methods for preparing, isolating, and manipulating various forms of nucleic acids are well known. (See for example, Berger and Kimmel, eds., *Guide to Molecular Cloning Techniques*, Academic Press, New York, N.Y. (1987); Sambrook, Fritsch and Maniatis, eds., *Molecular Cloning: A Laboratory Manual, 2nd Ed.*, Cold Spring Harbor Press, Cold Spring Harbor, N.Y. (1989).) Additionally, techniques for hyrbidization reactions are well known and a variety of kits are commercially available for nucleic acid manipulations.

In general, nucleic acids include polymers of deoxyribonucleotides (DNA) or ribonucleotides (RNA) and analogs thereof that are linked together by a phosphodiester bond. A polynucleotide can be a segment of a genome, a gene or a portion thereof, a cDNA, or a synthetic polydeoxyribonucleic acid sequence. Polynucleotides and nucleic acid polymers refer to polymeric forms of nucleotides and nucleotide analogs that comprise purine and pyrimidine bases, or other natural, chemically or biochemically modified, non-natural, or derivatized nucleotide bases, of any length. Polynucleotide and nucleic acid also refer to non-natural analogs of nucleic acids, such as peptide nucleic acids (nucleic acids with peptide backbones), and polyamide polynucleotides. An oligonucleotide is a polynucleotide having from 2 to 20 nucleotide monomer units.

A polynucleotide, including an oligonucleotide, (for example, a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide or oligonucleotide also can contain nucleotide analogs, including methylated nucleotides, non-naturally occurring synthetic nucleotides or modified naturally occurring nucleotides.

The covalent bond linking the nucleotides of a polynucleotide generally is a phosphodiester bond (the sugar-phosphate backbone). However, the covalent bond also can be any of a number of other types of bonds, including a thiodiester bond, an O-methyl phosphate, a phosphorothioate bond, a peptide-like amide bond or any other bond known to those in the art as useful for linking nucleotides to produce synthetic polynucleotides. The incorporation of non-naturally occurring nucleotide analogs or bonds linking the nucleotides or analogs can be particularly useful where the polynucleotide is to be exposed to an environment that can contain nucleolytic activity, since the modified polynucleotides can be less susceptible to degradation.

Electronic detection is the detection of a molecule through a measurement of voltage, resistance, and or current characteristics of an electronic sensor in the presence of the molecules to be detected. Optionally, the electronic signal measured in the presence of the molecule to be detected is compared to an electronic signal measured in the absence of the molecules to be detected.

A wafer refers to a semiconductor substrate used in the fabrication of integrated circuits and other microdevices and is for example a substrate comprised of a silicon crystal. The wafer serves as a substrate for a mircoelectronic device having a large number of electronic features that is built through the use of nano and microfabrication techniques such as deposition of various materials, such as conductors, semiconductors, and insulators, photolithographic patterning, etching, and ion implantation.

An array of electrodes can be equipped with circuitry for individually addressing the electrodes, driving the electrodes at selected voltages (or set current values corresponding to the desired voltage), memory for storing voltage current information to be supplied to the electrodes, memory and microprocessors for measuring electrode characteristics, differential amplifiers, field effect transistors (direct and floating gate). Alternatively, one or more of these functions can be performed by an attached computer system.

Electrode arrays are optionally used both to perform solid-phase synthesis of nucleic acids on the surface of the electrode and to detect the presence of single and double stranded nucleic acids on the surface of the electrode. For an electrode functionalized with a probe nucleic acid molecule exposed to a solution containing a target nucleic acid molecule, the presence of double stranded nucleic acids on the surface of the electrode is indicative of the occurrence of a hybridization reaction. Electronic detection provides the ability to monitor synthesis and hybridization reactions in real time without the use of labels. Since no wash is required to remove unbound labeled analytes, binding kinetics can be monitored using dynamic measurements at the solid-solution interface.

Figure 4:
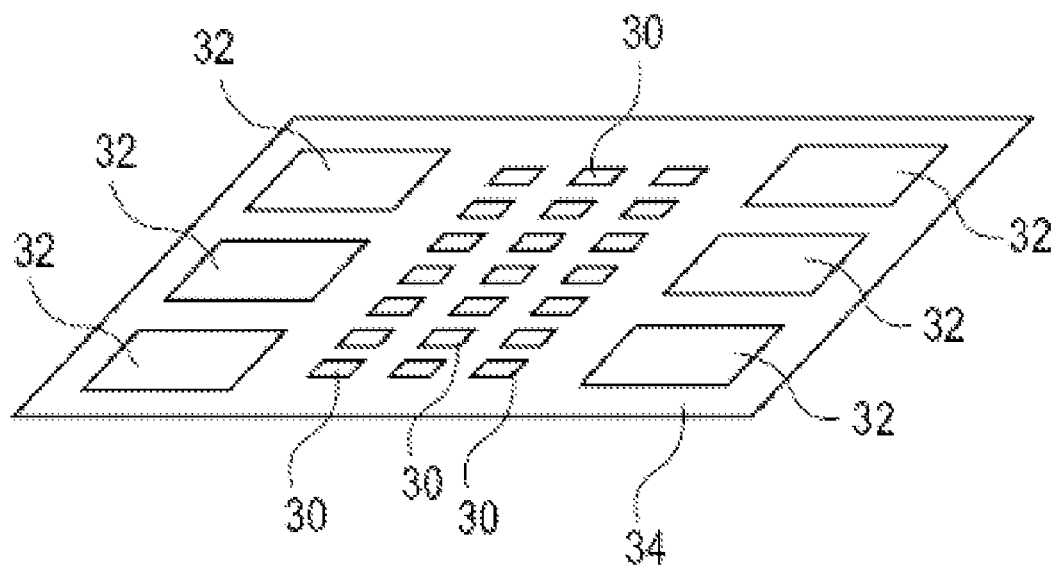
FIG. 4 is a simplified diagram of an exposed electrode array that can be used to synthesize polymers on the electrodes and to detect molecular recognition events using the array of electrodes.

FIG. 4 provides a simplified diagram showing an array of exposed sensing and reference electrodes 30 and drive electrodes 32 on a substrate 34. Nucleic acid probes (not shown) are attached to the sensing and or reference electrodes. The reference electrode may or may not have a similar or different affinity probes attached. The sensing electrodes optionally have a plurality of probe molecules attached and the probe molecules attached to one sensing electrode are different from the probe molecules attached to a different sensing electrode. Drive electrodes 32 are typically larger in surface area than the micron or sub-micron scale sensing and reference electrodes 30. Electronics associate with driving the electrodes and signal handling (sensing and referencing capacity) (not shown) are located in the substrate 34. An integrated charge value from an electrode is converted to a voltage value through a two stage amplifier. An internal (not exposed) monolithic NMOS or metal-insulator-metal capacitor is optionally connected to the amplifier via an internal switch and used as a reference capacitor.

Probe molecules can be attached to the surface of an electronic sensor according to a variety of methods. Additionally, the electronic sensing surface may be coated with thin layers of porous materials or with conducting polymers that facilitate the attachment of probes onto the surface of the sensor.

Optionally, an integrating charge amplifier is connected to an electrode (or the electrodes comprising the array) and configured to detect capacitance changes at the electrode surface. A differential amplifier (or a differential-input single-ended output amplifier) is a device that amplifies the difference between two input signals (−) and (+). Optionally, the integrating charge amplifier includes a drive circuit that is capable of providing voltage pulses which can be supplied, for example, as a square, sine, or sawtooth wave form to a solution-accessible (exposed) electrode. The integrating charge amplifier optionally also includes an input that is from an exposed sensing electrode and another input from a solution-exposed or unexposed reference electrode.

A device including one or more integrating charge amplifiers is preferably configured to measure the integrated charge and effective capacitance at the analyte-electrode interface. A change in integrated charge or effective capacitance can then be used to ascertain whether a hybridization reaction has occurred (i.e., whether analytes have bound at the electrode surface or to the affinity probe attached to the electrode surface). An array of integrating amplifiers and a corresponding electrode array are optionally fabricated on the same substrate. The substrate may also include synthesis and detection drive circuits, logic for switching, latches, memory, input/output devices.

Figure 5:
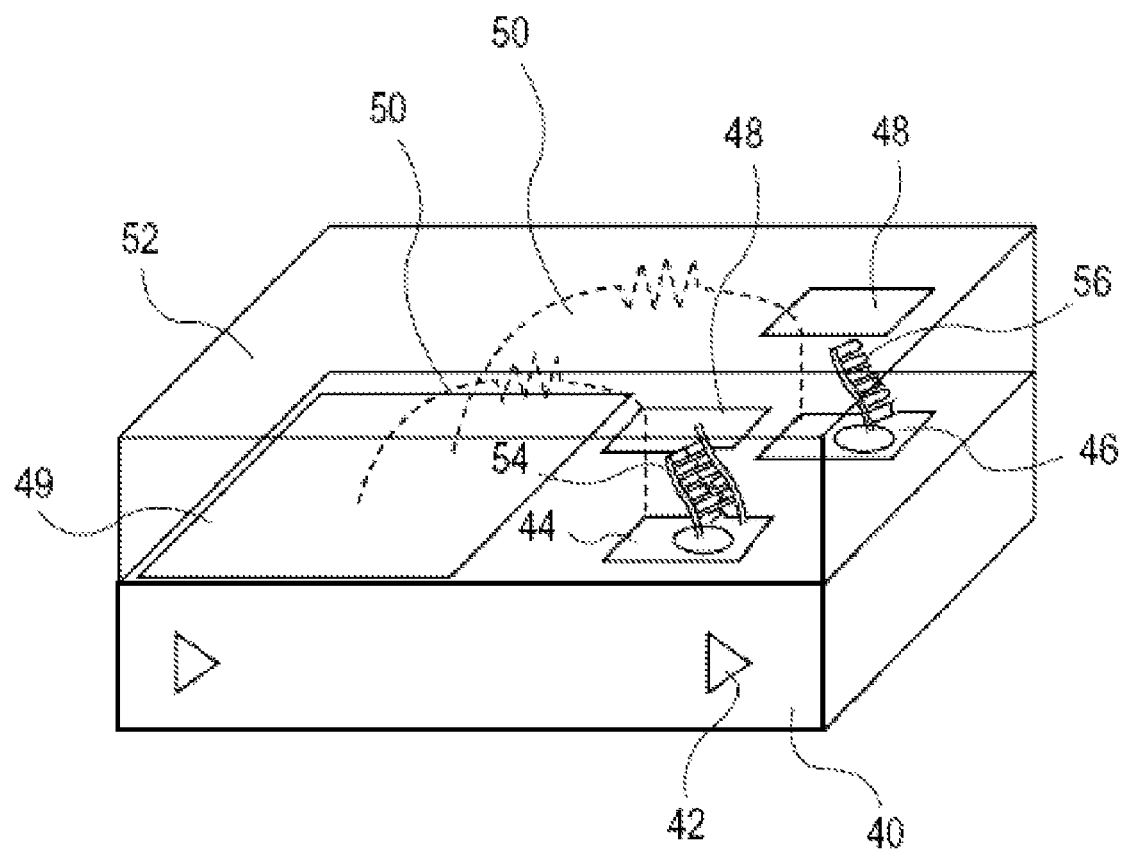
FIG. 5 provides a schematic of the electronic detection of a molecular recognition event using an array of exposed electrodes.

FIG. 5 provides a schematic of an exemplary electronic device capable of detecting a hybridization event between a surface-attached DNA probe molecule and a target molecule. The electronic molecular detection device has a substrate 40 that houses electronics for detecting 42 (as described more fully herein), exposed sensing electrodes 44, exposed reference electrode 46, and drive electrode 49. The electrodes 44, 46, and 49 are connected to electronics through physical electrical connections. In FIG. 5, dotted lines 50 demonstrate resistive and capacitive paths (virtual capacitive plates 48 are shown) established in the conductive matrix of buffer solution 52 and insulating affinity probe/analyte layer 54 on the electrode 44. The probe/analyte layer 54 is not to scale with respect to the electrode size and only one probe/analyte complex is shown (for simplicity) where many would typically be attached to an electrode surface. In FIG. 5, the electronic detection device can be operated in differential detection mode, in which both reference electrodes 46 and sensing electrodes 44 have attached affinity probes 54 and 56. The electronics 42 comprising a differential charge amplifier provide differential sensing data to an output amplifier and A/D or analog output.

For measurements of effective capacitance, the analyte is preferably provided in a conductive solution that provides a conductive path between the driving and the integrating electrodes of the amplifier. A conductive solution comprises for example, an aqueous solution having an ionic concentration or a conductive gel. A preferred method for operating a device including one or more integrating charge amplifiers includes providing a voltage pulse through the drive electrode to the conductive matrix. This pulse can be applied to the matrix with respect to an integrating electrode and the charge is accumulated on the integrating electrode over a fixed time.

Figure 6:
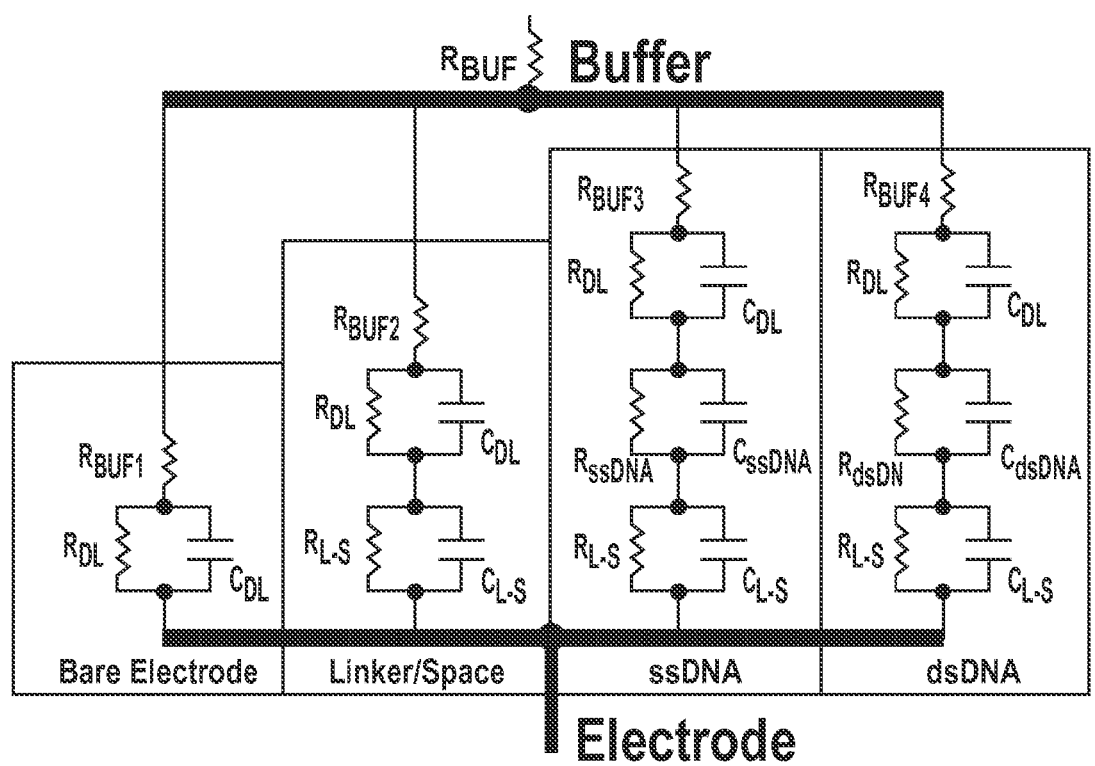
FIG. 6 shows a circuit model for the electronic detection of a molecular recognition event on an electrode.

The measured capacitance is established by the fixed sensing electrode, the dielectric formed by the attachment chemistry, attached probe, and bound analyte (if present), and a virtual parallel plate formed above the sense electrodes by the charge/ion distribution in the matrix. The measured capacitance is a function of the electrode area, the dielectric constant, and the distance of the virtual plate from the sensing electrode. Analytes binding to the electrode or the attached affinity probe will change the dielectric constant and or the distance between the virtual plate and the sensing electrode, thereby changing the effective capacitance and accumulated charge on the sensing electrode when a voltage is applied. The area and distance to the drive electrode are not material since the conductive matrix carries the voltage to the virtual plate. FIG. 4 provides a theoretical circuit model for the electronic detection of a hybridization reaction. In FIG. 6, ssDNA (single stranded DNA) represents the probe attached to the electrode and dsDNA (double stranded DNA) represents the probe hybridized to a target analyte. Any capacitance contributed by the drive electrode is in series with the measured capacitance and is small owing to the large electrode area.

Optionally, to compensate for noise that may be present (low frequency noise, thermal noise, etc.) a calibrating reference pulse is applied to an internal test capacitor to normalize the response of the amplifier during each measurement cycle. The output of this amplifier can then be digitized and post-processed. Post-processing comprises a software algorithm to remove random noise, slopes, or other artifacts from the data. Parameters can be determined experimentally by characterizing the various contributing parameters, such as electrode size, drive voltage, and environmental conditions such as temperature and analyte binding concentration.

Optionally, individually addressable sensing electrode arrays of various effective areas are created to increase the detection range of the amplifier to various concentrations of target in the solution. A large array of driving electrodes can be created to allow close coupling of driving voltage to the solution. Since the drive electrode capacitance is in series with the sense electrode plus probe or probe/target complex through the solution, preferably the driving electrode area is larger than the sensing electrode area to reduce parasitic effects. A system comprised of a large capacitor in series with a small capacitor is dominated by the small capacitor. In the case of a large capacitor in series with a small capacitor, $1/C_{series} = 1/C_{integrated} + 1/C_{drive}$ and this approaches $1/C_{integrated}$ in value as $C_{drive}$ gets large.

The exposed reference electrode allows for common mode noise rejection by inputting to one input the amplifier signal representing the same environmental conditions (pH, temperature, ion concentration, presence or absence of non-binding analytes, etc.). Alternatively, the reference capacitor can be exposed to air or covered to establish an absolute reference.

Figure 7:
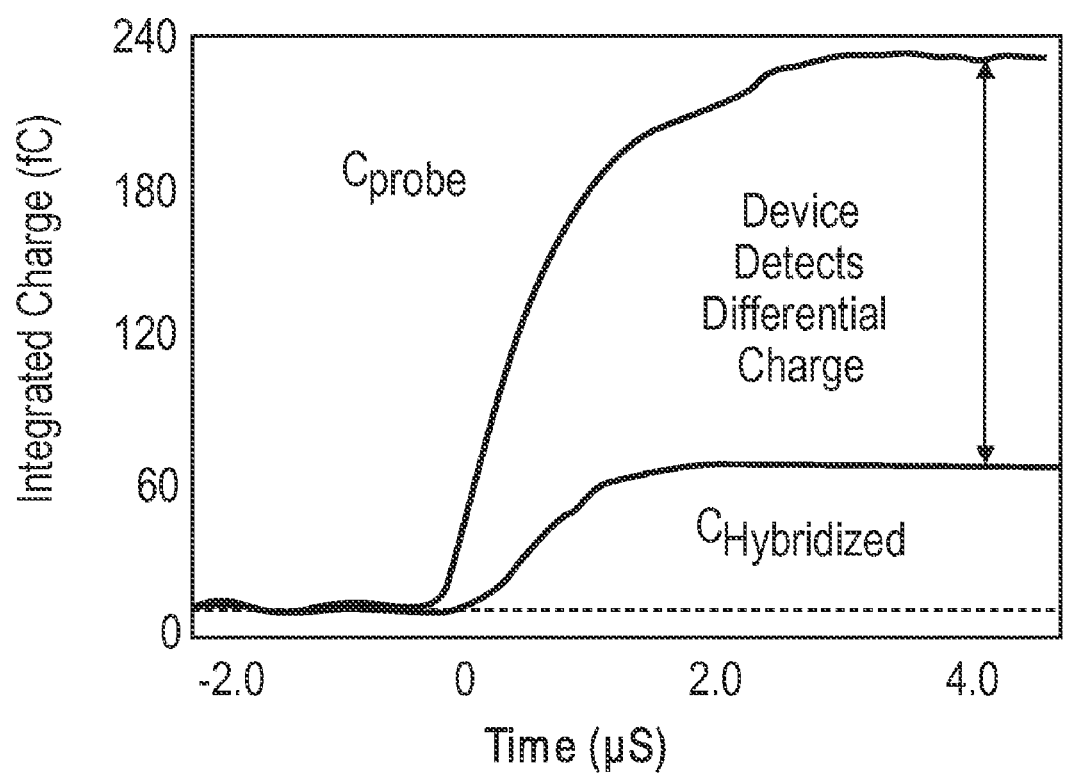
FIG. 7 provides a graph showing the electronic detection of a molecular recognition event, such as a DNA hybridization event, using exposed electrodes.

FIG. 7 provides graphs the operation of an exemplary device such as the exemplary devices shown in FIGS. 4 and 5 in the detection of a molecular recognition event at the surface of an electrode between a bound nucleic acid probe and a complementary nucleic acid molecule. FIG. 7 shows the measurement of integrated charge on two electrodes, the electrode having only the probe attached (trace labeled $C_{probe}$) and the electrode having an attached probe that is hybridized to a complementary nucleic acid (trace labeled $C_{hybridized}$). An integrating charge amplifier is used to detect capacitance on the functionalized electrode surface. A dynamic measurement at the solid-solution interface is obtained by applying a pulse to the functionalized electrode and integrating the current flow response over time as the capacitor discharges.

A pulse of voltage is applied to the solution with respect to an integrating electrode and charge is accumulated on the electrode over a fixed time. A calibrating reference pulse can be applied to the solution through an internal test capacitor to normalize the response of the amplifier during each measurement cycle. A two-stage integrating charge amplifier converts measured charge to voltage.

The measurement of change in capacitance at the sensing electrode can be accomplished in the following manner. The change can be detected with respect to the exposed reference capacitor when the reference electrode is exposed to the same solution as the sensing electrode. Optionally, a nucleic acid molecule that has similar electrical characteristics as the affinity probe attached to the sensing electrode but that does not bind to a target analyte in solution is attached to the reference electrode. A change in integrated charge is measured as binding occurs on the sensing electrode (binding to the probe attached on the sensing electrode) and no change is measured on the reference electrode. Alternatively, two measurements of the same electrode, before and after analyte binding, can be compared to determine the change in integrated charge resulting from target analyte binding. In this example, a measurement of the electrode at a previous time serves as the reference. Data is optionally gathered and analyzed using a computer.

In an additional alternative, the reference electrode can be configured to take direct capacitance measurements at the sensing electrode (non-differential mode). The reference electrode is covered with a dielectric substance (such as, for example, epoxy) or a dielectric layer (such as, for example, silicon dioxide) or left exposed to air. The signal from the electrode is compared to an open circuit thereby establishing an absolute reference for measurement.

The solution-accessible (or exposed) electrodes used in embodiments of the invention are made from metals, combinations of metals, or other conducting materials. For example, an electrode may be made from, for example, platinum, palladium, nickel, copper, iridium, aluminum, titanium, tungsten, gold, rhodium, as well as alloys of metals, conducting forms of carbon, such as glassy carbon, reticulated vitreous carbon, basal plane graphite, edge plane graphite, graphite, indium tin oxide, conducting polymers, metal doped conducting polymers, conducting ceramics, and conducting clays. A functionalized electrode is an electrode having a probe molecule that has a specific affinity for a target molecule attached to the electrode surface. An unfunctionalized electrode is an electrode having no probe molecule attached or an attached molecule that has no specific chemical affinity for a target molecule to be analyzed.

Electrodes are connected to sensing and driving circuitry according to known methods. For example, CMOS (complementary metal oxide semiconductor) circuitry could be used, magnetic radiation-addressable switches, direct connections from an electrode to a bond pad on the perimeter of a semiconductor chip, and or combinations thereof. Data is optionally gathered and analyzed using a computer.

Electrodes are connected to a source capable of providing voltage and current. For example, electrodes that form an array are connected to CMOS (complementary metal oxide semiconductor) switching circuitry, radio frequency (RF) and microwave addressable devices, light addressable devices, and or metal lines leading to the perimeter of the array. In embodiments of the invention, CMOS switching circuitry involves the connection of each of the electrodes to a CMOS transistor switch and provides the ability to individually address electrodes comprising an array. The switch is accessed by sending an electronic address signal down a common bus to SRAM (static random access memory) circuitry associated with the electrode. Radio and microwave frequency addressable switches involve the switching between on and off states through the use of a microwave or RF radiation. RF and microwave frequency switches can be tuned to receive a particular frequency or modulation frequency and switch without the use of array-based switching logic. Light addressable switches are moved between on and off positions by light in the ultraviolet through infra red frequency ranges. An electromagnetic signal can be spatially localized to provide switching.

A region of nucleic acid molecules on an electronic detection device may be created by a variety of methods. For example, the nucleic acid molecules may be placed into a solution and spotted onto the surface of the electronic detection device. Spotting systems that allow a plurality of solutions to be spotted onto an array in a controlled manner are commercially available, form for example, Agilent Technologies, Santa Clara, Calif.

An array of nucleic acids can also be created using in situ synthesis methods. For example, the synthesis of an array of nucleic acid polymers on a substrate can be accomplished using photochemical synthesis methods, photoresist synthesis methods, and electrochemical synthesis methods. In photochemical synthesis techniques, protecting groups that prevent polymer growth are removed photochemically using light energy (electromagnetic radiation).

In photoresist synthesis methods, a photoresist is applied over the array synthesis area and the photoresist is patterned with electromagnetic radiation to expose areas in which the polymer chain is to be extended by monomer addition or to protect regions in which the polymer chain is not to be extended from monomer addition. In an exemplary synthesis method, photoresists such as poly(methyl methacrylate) (PMMA) are provided with sulfonium, polonium, or halonium salts that generate an acid upon exposure to UV light. The photo-chemically generated acid deprotects the protected polymer chain (for example, through the removal of a DMT group) to allow the addition of a monomer to the growing end of the unprotected polymer chain. Optionally, the photoresist layer also includes a photosensitizer, such as a benzophenone, a thioxanthenone, an anthraquinone, a fluorenone, an acetophenone, or perylene. In the case of a photosensitizer, the generation of the protecting group removal reagent may occur through the absorption of light by a photosensitizer followed by reaction of the photosensitizer with the protecting group removal reagent precursor (the molecule capable of generating an acid upon activation), energy transfer from the photosensitizer to the cleavage reagent precursor, or a combination of two or more different mechanisms. After the photoresist is removed, the polymer chain in the light-exposed regions is available for monomer addition. Through repeated cycles of photoresist coating, light exposure (optionally through a mask to pattern the photoresist), and monomer addition, an array of polymers is built on the surface of a substrate.

Figure 8:
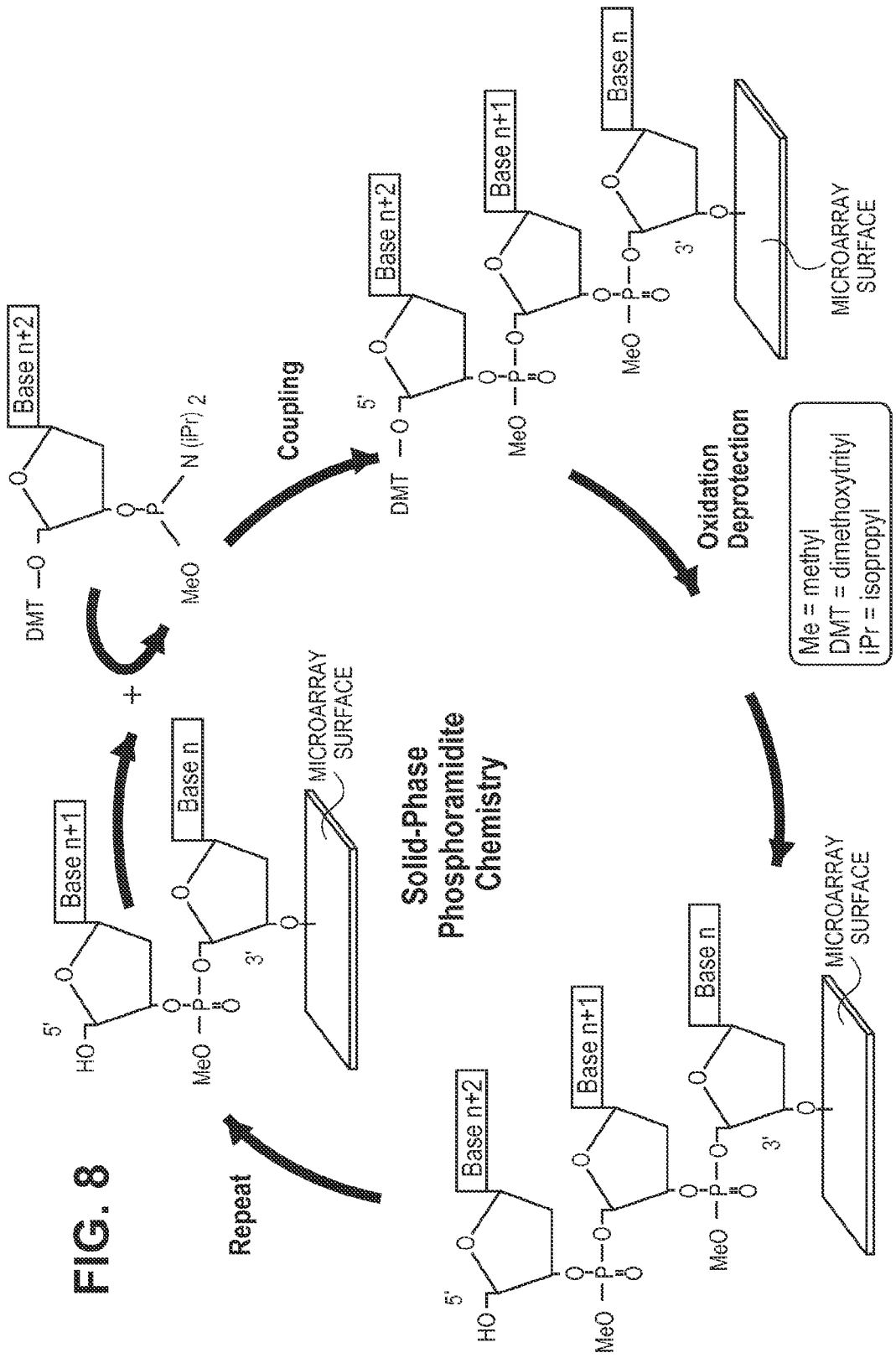
FIG. 8 diagrams a method for solid-phase nucleic acid synthesis that can be used to controllably build nucleic acid molecules having a desired sequence on a solid surface.

A monomer addition cycle is a series of chemical reactions that result in the addition (or covalent attachment) of a monomer to a growing polymer chain or linker molecule. For example, the following steps typically comprise a common method used to synthesize a polynucleotide on a solid support (i.e., phosphoramidite-based solid phase polynucleotide synthesis). Referring now to FIG. 8, a first step in the polynucleotide synthesis is the deprotection of the surface-attached polymer growth site through removal of the DMT group from, for example, a 5'-protected nucleotide wherein the 5'-hydroxyl is blocked through the covalent attachment of DMT. The deprotection is accomplished using a protic acid (for example, a protic acid such as trichloroacetic acid, dichloroacetic acid, or an electrochemically generated acid). The substrate optionally is then washed to remove the cleaved protecting group and other reagents and mobile reaction products (with, for example, acetonitrile). A molecule, such as a phosphoramidite nucleotide, optionally activated with tetrazole, is then coupled to the surface-attached deprotected molecule. Optionally unreacted surface-attached deprotected molecules are capped to prevent further participation in subsequent monomer addition cycles. The trivalent phosphate trimester linkage is converted to a pentavalent phosphate triester through oxidation with, for example, iodine, and the pentavalent phosphate triester is converted to a phosphodiester through reaction with ammonium hydroxide.

A protecting group is a chemical functional group that is designed to block a reactive site in a molecule, but that may be removed upon exposure to an activator or a deprotecting reagent. When the protecting group is removed, the reactive site is more readily available to react and form chemical bonds. A deprotecting agent is an agent that can remove a protecting group from a molecule leaving the reactive site available for further chemical reaction. Deprotecting reagents include, for example, acids, bases, free radicals, and electromagnetic radiation. Protecting groups can be bound to a monomer, a polymer, a linker molecule or a monomer, or polymer, or a linker molecule attached to a solid support to protect a reactive functionality on the monomer, polymer, or linker molecule. Hydroxyl groups on phosphoramidites may be protected by dimethoxytrityl (DMT), which is acid labile (removable). Exocyclic amine groups on nucleotides, in particular on phosphoramidites, are preferably protected by dimethylformamidine on the adenosine and guanosine bases, and isobutyryl on the cytosine bases, both of which are base labile protecting groups. This protection strategy is sometimes known as fast oligonucleotide deprotection (FOD).

Any unreacted deprotected chemical functional groups may be capped at any point during a synthesis reaction to avoid or to prevent further bonding at the selected molecule. In general, capping reagents are agents that prevent further chain growth at the site of polymer chain formation such as, for example, an acid anhydride without further reactive functionalities. Capping groups cap deprotected functional groups by, for example, binding with the unreacted amino functions to form amides. Capping agents suitable for use in an embodiment of the invention include: acetic anhydride, n-acetylimidizole, isopropenyl formate, fluorescamine, 3-nitrophthalic anhydride and 3-sulfoproponic anhydride.

Electrochemical reagents are reactive species that can be generated electrochemically at an electrode through an oxidation or reduction process. Electrochemical reagents can be generated at an electrode by supplying a minimum voltage that corresponds with the oxidation or reduction potential of the desired species in solution. Reagents that are acids ($H^+$) and bases (such as $OH^-$) can be generated electrochemically. Molecules that can be used to generate an acid electrochemically (EGAs) that can used to deprotect a growing nucleic acid polymer attached to an electrode surface (e.g., remove a DMT group) include, for example hydroquinone that is converted to benzoquinone upon oxidation thereby releasing two protons ($H^+$) and a hydroquinone that is converted to anthraquinone upon oxidation thereby releasing two protons ($H^+$) (a non-aqueous system).

An electrochemical reagent can be generated at a solution-accessible electrode by applying sufficient electrical potential to an electrode. The electrochemical reagent is capable of removing a protecting group from the growing end of a polymer being synthesized on the electrode. In hydroquinone/benzoquinone example, the electrochemical reagent produced ($H^+$) is a deprotecting agent. In other reactions, the electrochemical reagent may be an intermediate in the formation of the deprotecting agent.

The electrodes of the array optionally are also used to synthesize polymers. For synthesis the electrodes are used to create an acidic or basic region around the electrode surface. The acid or base causes deprotection of the growing polymer chain and allows monomer addition. Optionally, confinement electrodes of opposite polarity or floating separate attachment electrodes are provided to confine the acid or basic region produced and prevent drift to surrounding electrodes that may not be activated for synthesis. Further optionally, a set of two latches are provided at each electrode capable of being activated for polymer synthesis to allow the electrode to exist in multiple states: driven by a first voltage, driven by a second voltage, or floated during the synthesis cycle.

Voltage sources for the electrodes can be internally multiplexed from external source(s) through digital control and can optionally be applied in parallel to a large array of electrodes. In operation, voltages are applied to a programmed selection of electrodes in the presence of an acid-generating reagent (EGA) as a solution containing a monomer is supplied to the exposed electrodes. The applied voltage creates an acidic region and allows polymer growth at the selected electrode. Through selection of electrodes and choice of monomer to supply, polymers of known desired sequence are synthesized at the electrodes.

EXAMPLES

Functionalization of a $SiO_2$ surface with a trifunctional linker: A silicon dioxide substrate is washed with piranha solution at room temp for 1 hour, rinsed with de-ionized water three times, and air dried. A trifunctional linker molecule, 1,1-diDMT-oxygen-3-phosphoramidite propane is dissolved in acetonitrile and is then added onto the silicon dioxide surface and allowed to react for 30 min. at room temperature. DMT is deblocked with trichloroacetic acid room temperature for 20 min. and the surface is treated with DMT protected polyethyleneglycol phosphoramide in acetonitrile for 30 min. at room temperature.

Synthesis of a trifunctional linker: A sugar molecule having multiple hydroxyl groups, two of which are protected by a DMT protecting group, one is transformed into phosphoramidite by using 2-cyanoethyl-N,N-diisopropylchlorophosphoramidite, diisopropylethylamine, THF, −78 to 25° C. The other hydroxyls are capped with acetic anhydride. The sugar molecule is a pentose, hexose, or heptose, such as arabinose, ribose, ribulose, zylose, xylulose, lyxose, allose, altrose, fructose, galactose, glucose, gulose, idose, mannose, sorbose, talose, tagotose, sedoheptulose. Reagents are purchased from Sigma-Aldrich, St. Louis, Mo.

The invention claimed is:

1. An array of DNA molecules on a substrate comprising, a substrate that has a surface wherein the surface comprises regions and the regions comprise a plurality of DNA polymers attached to the surface of the substrate, wherein at least one region comprise a plurality of DNA polymers that are attached to first trifunctional linkers such that at least two DNA polymers are attached to one first trifunctional linker, wherein the first trifunctional linkers have three sites for attachment, wherein a first of the two DNA polymers is attached to one of the three sites of the first trifunctional linker, a second of the two DNA polymers is attached to a second of the three sites of the first trifunctional linker, and a third site of the first trifunctional linker is attached to a second trifunctional linker, wherein the second trifunctional linker has three sites for attachment, and wherein a first trifunctional linker is attached to one of the three sites of the second trifunctional linker, another first trifunctional linker is attached to a second of the three sites of the second trifunctional linker, and a third site of the second trifunctional linker is attached to the surface of the substrate, and wherein the trifunctional linker is a molecule according to the structure:

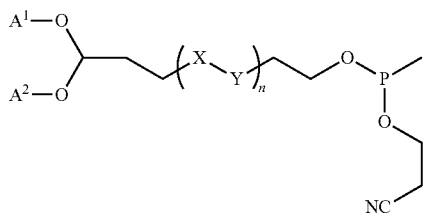

wherein when X and Y are different, X and Y are selected from the group consisting of $CH_2$, $CHR^1$, phenyl, O, S, NH, and $NR^2$, and in the case where X and Y are the same X and Y are selected from the group consisting of $CH_2$, $CHR^2$, and phenyl wherein $R^1$ is selected from the group consisting of —OH, —$CH_3$, —$CH_2OH$, —$CH_2CH_3$, and —$CH_2CH_2OH$ and $R^2$ is selected from the group consisting of —$CH_3$, —$CH_2CH_3$, and —$CH_2CH_2CH_3$, n is an integer from 0 to 10, and $A^1$ and $A^2$ are DNA polymers.

2. The array of claim 1 wherein the array comprises 1,000 to 10,000 regions.

3. The array of claim 1 wherein the array comprises 100 to 1,000 regions.

4. The array of claim 1 wherein a region of the array is less than 100 µm$^2$.

5. The array of claim 1 wherein the DNA polymers each comprise from 5 to 50 nucleic acids.

6. The array of claim 1 wherein the DNA polymers each comprise from 10 to 30 nucleic acids.

7. The array of claim 1 wherein the DNA polymers include a spacer group and are attached to the first trifunctional linker through the spacer and the spacer group comprises a polyethylene glycol.

8. The array of claim 1 wherein the regions additionally comprise electrodes.

9. The array of claim 8 wherein the electrodes comprise platinum.

10. The array of claim 1 wherein the DNA polymers each comprise from 5 to 50 nucleic acids.

11. The array of claim 1 wherein n is an integer from 0 to 5.

12. The array of claim 1 wherein the regions comprise electrodes.

13. The array of claim 1 wherein the regions comprise platinum metal.

14. The array of claim 1 wherein $A_1$ and $A_2$ comprise a DNA polymer and a spacer.

* * * * *